United States Patent
Bokros et al.

(10) Patent No.: US 8,303,652 B2
(45) Date of Patent: Nov. 6, 2012

(54) HEART VALVE INSERTER

(75) Inventors: Jack C. Bokros, Austin, TX (US);
Jonathan C. Stupka, Austin, TX (US);
C. Thomas Waits, Pflugerville, TX (US)

(73) Assignee: On-X Life Technologies, Inc., Austin, TX (US)

( * ) Notice: Subject to any disclaimer, the term of this patent is extended or adjusted under 35 U.S.C. 154(b) by 1476 days.

(21) Appl. No.: 11/568,259

(22) PCT Filed: Jan. 23, 2006

(86) PCT No.: PCT/US2006/002363
§ 371 (c)(1),
(2), (4) Date: Oct. 24, 2006

(87) PCT Pub. No.: WO2006/081213
PCT Pub. Date: Aug. 3, 2006

(65) Prior Publication Data
US 2007/0219629 A1    Sep. 20, 2007

Related U.S. Application Data

(60) Provisional application No. 60/650,778, filed on Jan. 27, 2005.

(51) Int. Cl.
*A61F 2/24* (2006.01)
(52) U.S. Cl. ...................... 623/2.11; 623/1.26
(58) Field of Classification Search .................. 623/1.26, 623/2.1, 2.11
See application file for complete search history.

(56) References Cited

U.S. PATENT DOCUMENTS

| 3,491,757 A | 1/1970 | Arce |
| 4,585,453 A | 4/1986 | Martin et al. |
| 4,683,883 A | 8/1987 | Martin |
| 5,236,450 A | 8/1993 | Scott |
| 5,443,502 A | 8/1995 | Caudillo et al. |
| 5,908,452 A | 6/1999 | Bokros et al. |
| 5,984,959 A | 11/1999 | Robertson et al. |
| 6,287,339 B1 | 9/2001 | Vazquez et al. |
| 6,319,280 B1 | 11/2001 | Schoon |

FOREIGN PATENT DOCUMENTS

SU    1690738 A1 * 11/1991

OTHER PUBLICATIONS

Japanese Patent Office, Official Notice of Rejection mailed Feb. 17, 2012 in Japanese application No. 2007-553164.
Japanese Patent Office, Official Notice of Rejection mailed Apr. 26, 2011 in Japanese application No. 2007-553164.

* cited by examiner

*Primary Examiner* — David H Willse
*Assistant Examiner* — Javier Blanco
(74) *Attorney, Agent, or Firm* — Trop, Pruner & Hu, P.C.

(57) ABSTRACT

A heart valve holder-inserter (21, 121) is designed to facilitate easy implantation of a mechanical heart valve prosthesis (23, 123). This holder-inserter, at its distal end, incorporates a pair of diametrically opposed guide members (47, 49, 81, 147, 149) which extend well beyond the leading edge of the prosthesis and which have exterior surfaces (53, 83, 153) of substantial dimension that are smoothly curved and proportioned so as to slowly spread the tissue annulus in order to facilitate easy entrance thereinto of the leading edge portion of the mechanical valve body.

8 Claims, 5 Drawing Sheets

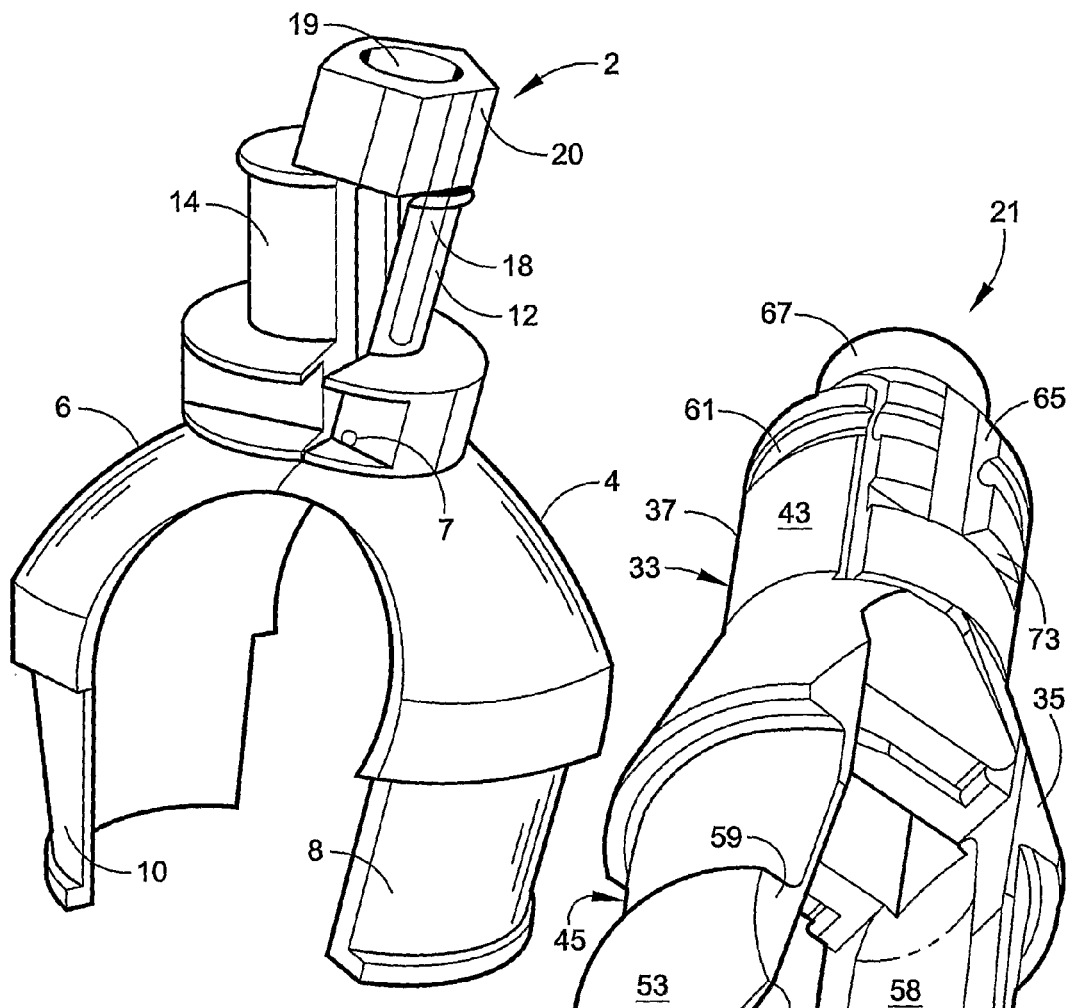
FIG. 1 PRIOR ART
FIG. 2
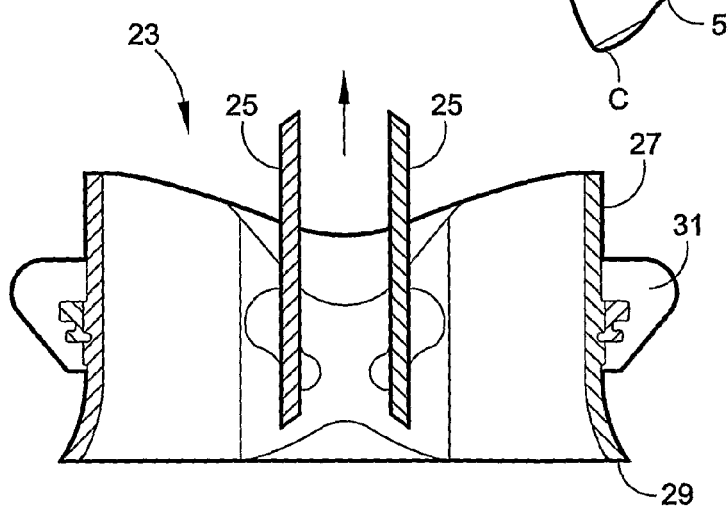
FIG. 3

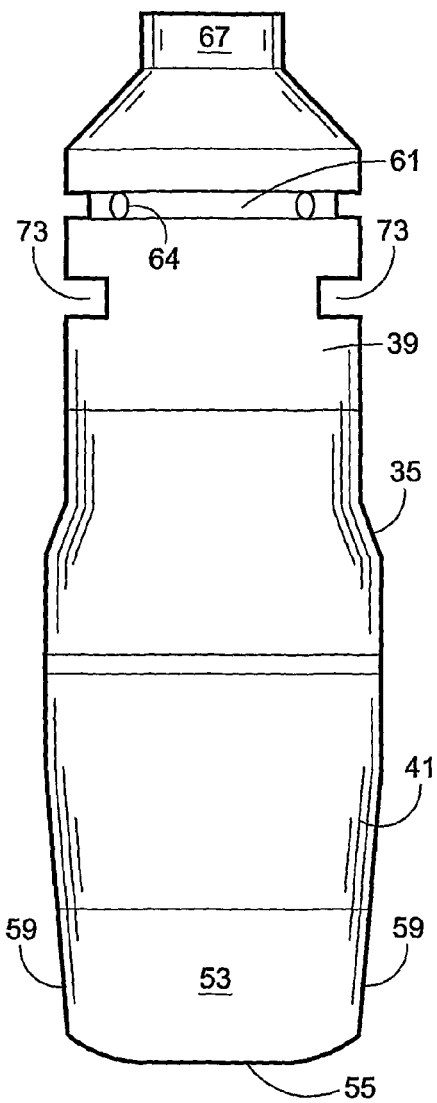
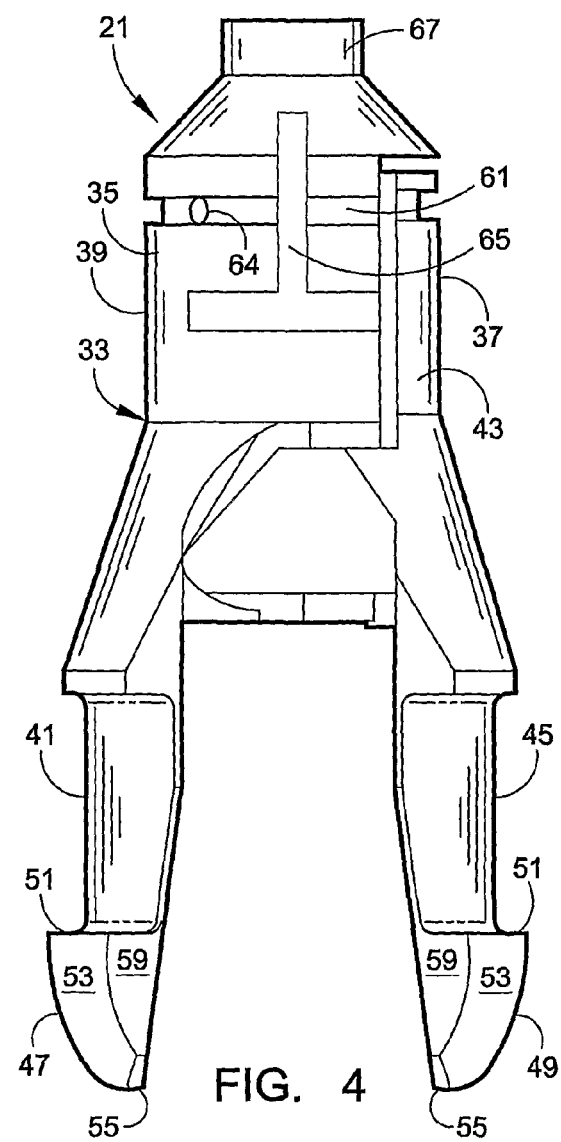
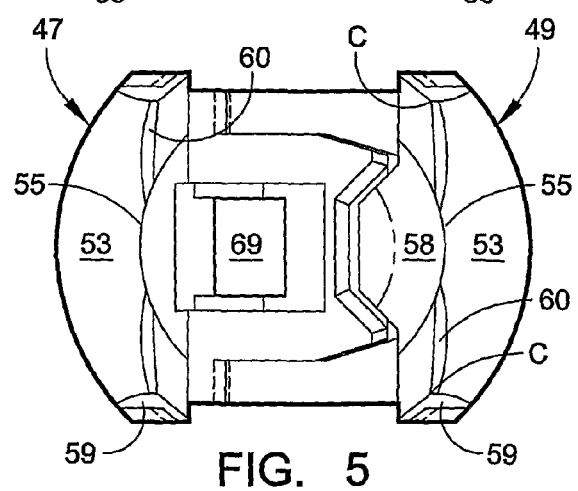
FIG. 6
FIG. 4
FIG. 5

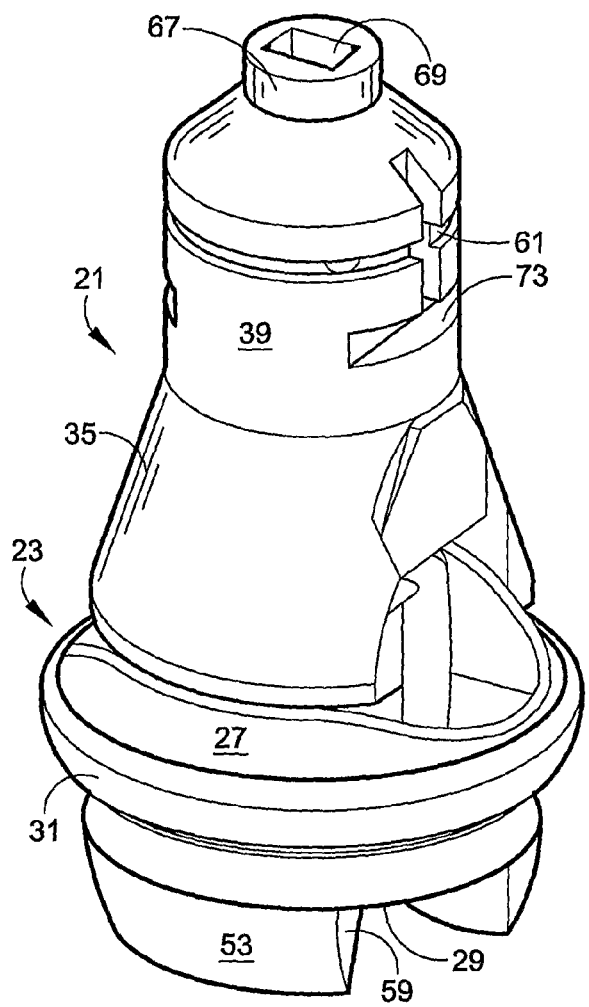
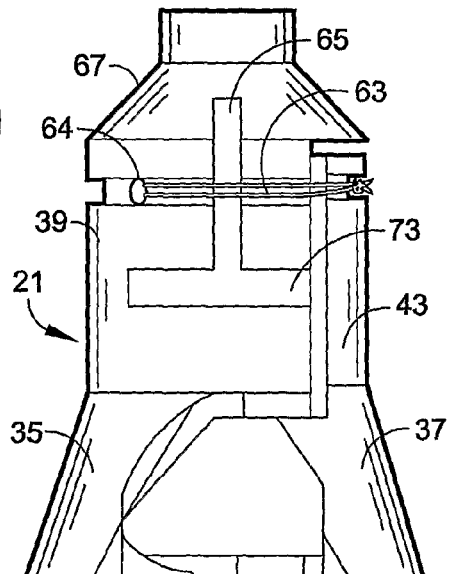
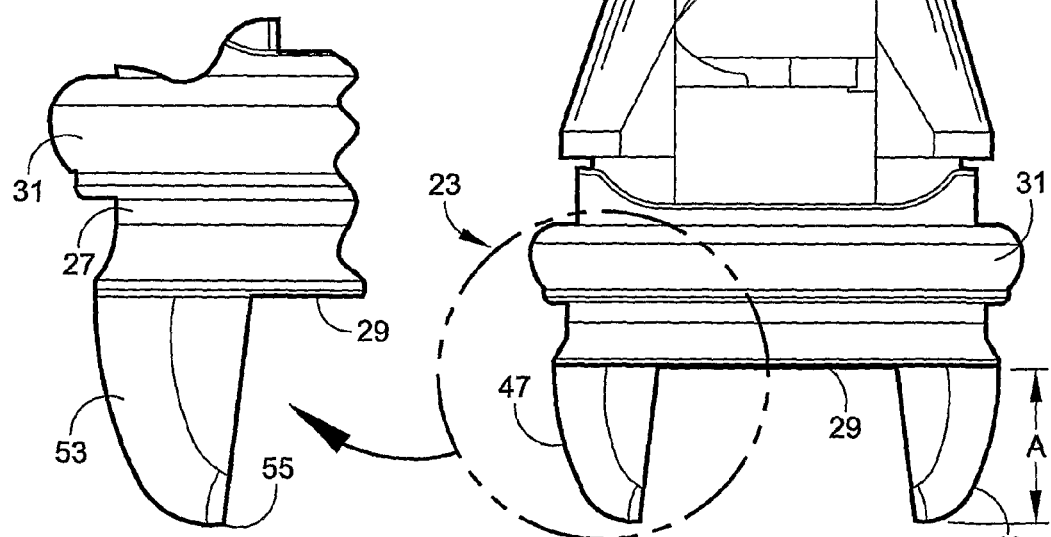
FIG. 7
FIG. 8A
FIG. 8

HEART VALVE INSERTER

This application claims priority from U.S. Provisional Patent Application Ser. No. 60/650,778, filed Jan. 27, 2005.

The present invention relates to a device for holding and inserting a mechanical heart valve prosthesis and more particularly to a device of this type which facilitates the insertion of an aortic heart valve.

BACKGROUND OF THE INVENTION

The use of surgically implanted mechanical heart valves has become widespread throughout the world and even routine in many countries. There are a variety of mechanical heart valves that have become well-accepted for use in the United States, Europe and Japan as well as in other countries throughout the world, one of which is sold as the On-X heart valve by Medical Carbon Research Institute, LLC, the assignee of this application. This mechanical heart valve prosthesis is shown in U.S. Pat. Nos. 5,545,216, 5,641,324, 5,772,694 and 5,908,452, for example.

Special tools have been developed to assist in the implantation of mechanical heart valves of this general type. It is important that an effective tool should be capable of holding the valve and facilitating its manipulation at the implantation site in order to properly position it.

Shown in FIG. 1 is a prior art valve holder 2 of the type often used for implanting a mechanical heart valve in 1992 and earlier. The valve holder 2 consists of two parts which are generally symmetrical to one another, a first or front part 4 and a second or back part 6. The prior art valve holder 2 is illustrated in FIG. 1 in an open condition. The two main body parts of the holder are hinged in some fashion, as example, by a pin 7 or by a living hinge. Two legs 8 and 10 are configured to press outward against an inside wall of an annular valve body when front and rear upper shaft sections 12, 14, respectively, are held together, which is often accomplished by a knotting a flexible tie. The front upper section 2 also has a longitudinal slot 18 which aids in cutting the tie, and it may have a transverse bore through which the tie is threaded and knotted so it remains associated with the inserter and is removed with it following implantation. The distal end of a handle (not shown) is usually received in a cavity or receptacle 19 formed in a cap portion 20 that surmounts the front part 12 of the holder, and the handle is secured in a conventional manner.

Reference is also made to the above-described inserter in U.S. Pat. No. 5,236,540 entitled "Heart Valve Holder-Rotator". This patent illustrates and describes a similar inserter where the main body of the holder is formed with a pair of opposed hinged side sections which have depending legs that move toward and away from each other in a manner similar to the two hinged parts described above, but both legs pivot with respect to a central portion of the body. Another heart valve holder of this general type is shown in U.S. Pat. No. 5,443,502.

Whereas these heart valve holders do securely engage a heart valve prosthesis so as to allow it to be positioned and rotated, oftentimes it is difficult to facilitate the passage of the leading end of the heart valve prosthesis through the annulus in the heart of the patient where the damaged natural valve leaflets were excised. It has been found that this may be a particular problem during the aortic valve replacement when the surgeon must work through the immediately upstream portion of the aorta. Accordingly, improvements in these tools for handling and implanting heart valves have been sought.

SUMMARY OF THE INVENTION

The invention provides a heart valve holder-inserter that includes a main body that is formed with a pair of sloping guide members at its distal end which extend longitudinally in a direction opposite to the direction in which the handle extends. The guide members have tips that are diametrically spaced apart a distance less than the corresponding dimension of a leading portion of a heart valve that would be releasably carried thereon. This design allows the heart valve carried by the holder to be smoothly inserted into the annulus and spread the tissue orifice to facilitate passage therethrough of the leading portion of the heart valve by engaging the tissue over a substantial area and slowly forcing it outward. The holder-inserter is found to be particularly advantageous in inserting an aortic valve, and even more advantageous in inserting an aortic valve having the construction shown in the aforementioned '452 patent where the entrance into the valve body flares outward, thus presenting a rim having an exterior concave, toroidal surface which is designed to seat against the inward facing surface of the heart tissue annulus.

In one particular embodiment, the invention provides a device for inserting a prosthetic heart valve into an annulus of the heart of a patient, which device comprises a main body proportioned for releasable engagement with a prosthetic valve, said main body having means for connection to a handle for moving and positioning the main body and the valve engaged therewith; and said main body also having two sloping guide members extending longitudinally from said main body in a direction generally opposite that in which said handle extends, which guide members have tips which are diametrically spaced apart a distance less than a corresponding dimension of a leading portion of a heart valve that would be releasably carried thereon, with outward-facing surfaces of said guide members sloping from said tips outward to about a diameter of the valve leading portion, whereby passage of the leading portion of the valve prosthesis into an annulus, from which the patient's defective valve leaflets have been excised, is facilitated.

BRIEF DESCRIPTION OF THE DRAWINGS

FIG. 1 is a perspective view of a prior art tool for holding and inserting a mechanical heart valve prosthesis.

FIG. 2 is a perspective view of a heart valve holder-inserter embodying various features of the present invention.

FIG. 3 is a cross-sectional view showing a mechanical heart valve prosthesis of the type generally marketed as the On-X aortic valve and disclosed in the '452 patent.

FIG. 4 is a front view of the holder-inserter shown in FIG. 2.

FIG. 5 is a bottom view of the holder-inserter shown in FIG. 4.

FIG. 6 is a left side view of the holder-inserter shown in FIG. 4.

FIG. 7 is a perspective view of an assembly of the holder-inserter shown in FIG. 2 with a mechanical heart valve engaged thereon.

FIG. 8 is a front view of the assembly shown in FIG. 7.

FIG. 8A is a fragmentary enlarged view of FIG. 8.

DETAILED DESCRIPTION OF THE PREFERRED EMBODIMENTS

Figure 10:
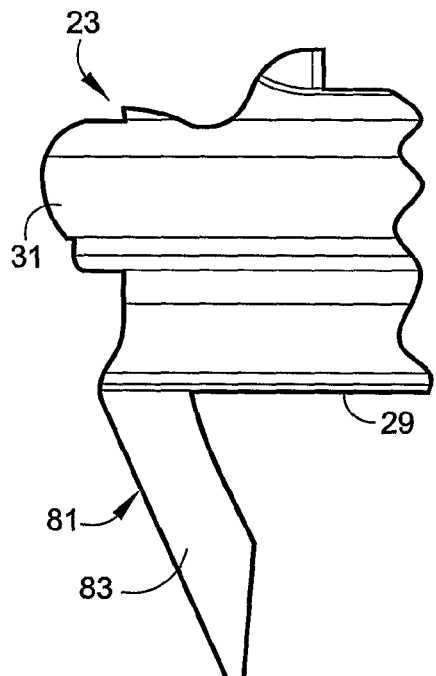
FIG. 10 is a fragmentary view similar to FIG. 8A showing an alternative embodiment of a heart valve holder-inserter embodying various features of the invention assembled with the FIG. 3 heart valve.
Figure 9:
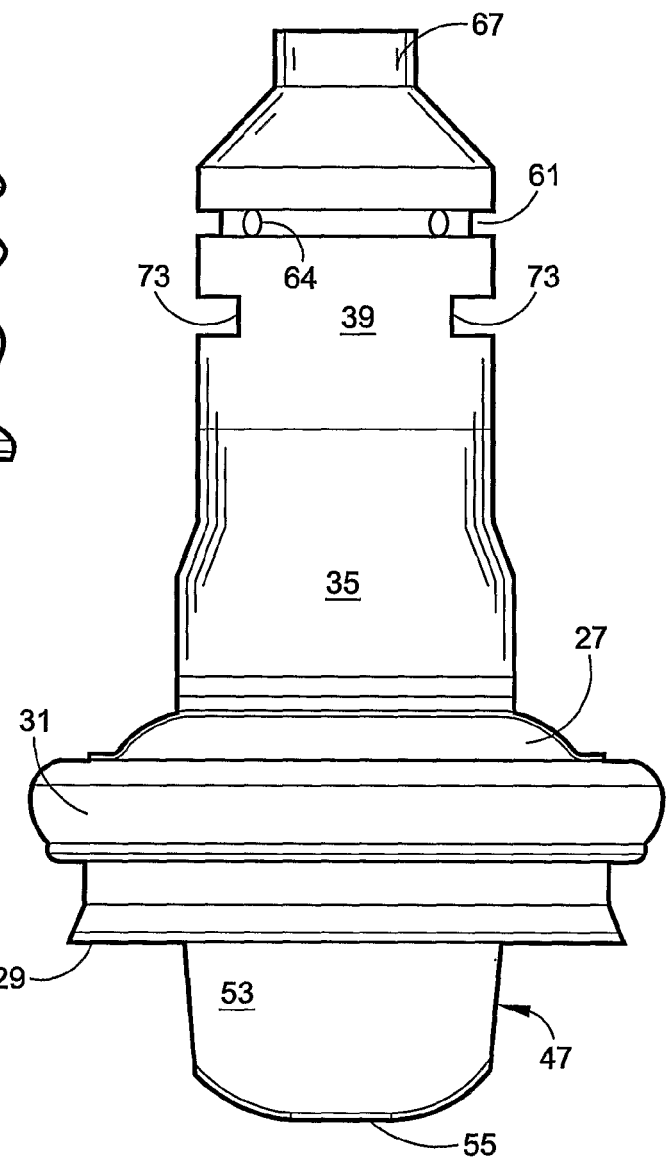
FIG. 9 is a side view of the assembly shown in FIG. 7.

The invention provides a device 21 which serves as a holder-inserter for implanting a mechanical heart valve prosthesis in an annulus in the human heart. The principles embodied in the device 21 are effective in creating a useful holder-inserter suited for implanting a wide variety of mechanical heart valves, particularly bileaflet heart valves; however, the preferred embodiment of the device that is shown in the drawings is proportioned and shaped to facilitate the implantation of the On-X heart valve 23, a cross-sectional view of which is illustrated in FIG. 3. This valve 23 employs a pair of leaflets 25 that are pivotally mounted on a valve body or orifice ring 27, as described in detail in the earlier mentioned US patents, which valve body 27 has an outwardly flaring entrance end 29. The illustrated valve 23 is designed to be inserted as an aortic valve replacement where it will be positioned so that the concave, generally toroidal exterior surface of the curved entrance end 29 lies in contact with the tissue annulus from which leaflets of the defective natural valve were excised. The implanted prosthesis is secured in place by suturing through a sewing ring 31 which is affixed to a central exterior region of the valve body 27, with sutures being secured by pledgets which are positioned on the heart side of the annulus, i.e. facing the left ventricle of the heart.

The holder-inserter device 21 has a main body 33 which comprises two hinged parts that are movable relative to each other. These are arbitrarily referred to as a front part 35 and a rear part 37. The body can be made of any acceptable material as well known in this art, but will usually be molded from polymeric material capable of being sterilized, such as nylon, Teflon, Delrin or polysulfone. The two parts 35, 37 may be molded separately and suitably joined at a pivot or hinge point therebetween. Alternatively they may be molded as a single integral piece being interconnected by a living hinge. The front or left hand part 35 (as oriented in FIG. 4) is formed with an upper section 39 and a depending leg 41. The rear or right hand part 37 is formed with an upper section 43 and a depending leg 45. The two legs 41 and 45 have the same construction, being mirror images of each other; the recessed upper portions of the legs constitute a groove proportioned to receive valve body 27 to be carried thereupon.

The main body 33 is molded as two separate pieces with a hinge point therebetween which is established in any suitable manner. For example, a separate hinge pin can be seated in bores provided in both parts 35, 37, or short stub pivots can be seated in receptacles molded in the mating part. The two parts will pivot between their engaging orientation (as illustrated in FIGS. 2 and 4) and a release orientation (such as that shown in the FIG. 1) wherein one leg 45 has swung closer to the other leg 41 so as to release a mechanical heart valve with which it was earlier engaged.

The heart valve holder-inserter 21 generally resembles the prior art device depicted in FIG. 1 except for the incorporation of a pair of sloping guide members 47, 49 which are respectively located at the lower ends of the legs 41, 45 and formed integrally therewith. Each guide member has a transverse surface or a flange 51 formed at its upper end against which the leading edge 29 of the mechanical heart valve seats; this engagement secures the valve in place on the holder-inserter 21 when the two body parts 35, 37 are in the engaging orientation, as depicted in FIG. 4 and FIG. 7, for example.

The guide member 49 is formed with a sloping exterior surface 53 that smoothly extends from the outer edge of the flange 51 down to a tip 55. When the two legs 41, 45 are in their engaging position, the outer edge of the transverse surface 51 lies close to the outer edge of the rim 29 of the heart valve, as best seen perhaps in FIG. 8 where the inserter 21 is illustrated with a heart valve 23 engaged thereon. The longitudinally sloping surface 53 extends smoothly over the entire distance from the edge of the ledge to the lower or bottom tip 55, which is described as being a continuous curve, i.e. having no reentrant section. In FIG. 8, the outer edges of the tips 55 are spaced apart at their greatest distance, a distance which is substantially less than the diameter of the rim 29 of the heart valve at its leading edge, preferably a distance between about 30% and 80% of the diameter of the rim and more preferably between about 50% and 65% of the diameter of the rim. Preferably these outer edges are arcs which lie on a circle which has its center on the longitudinal axis of the inserter 21; however, such is not a requirement as explained hereinafter.

Figure 11:
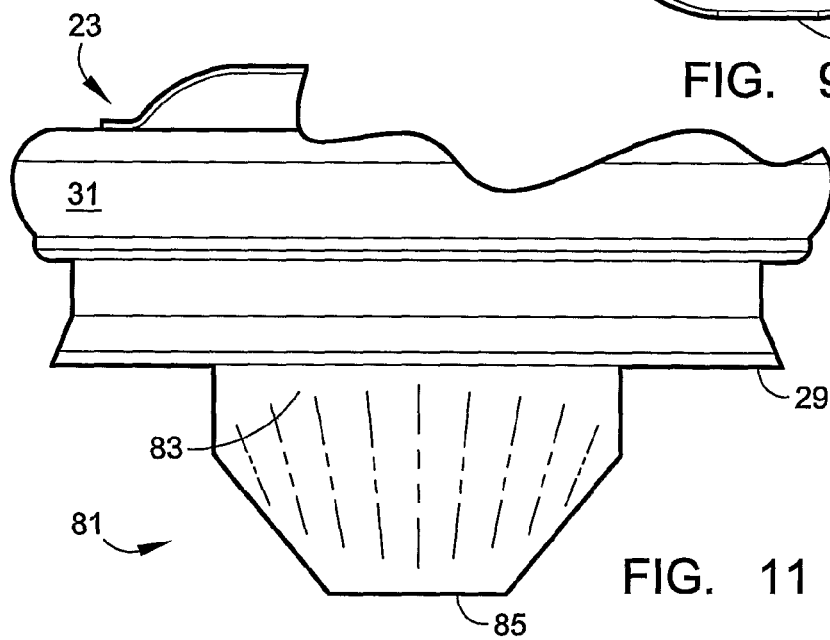
FIG. 11 is a fragmentary left side view of the assembly shown in FIG. 10.
Figure 12:
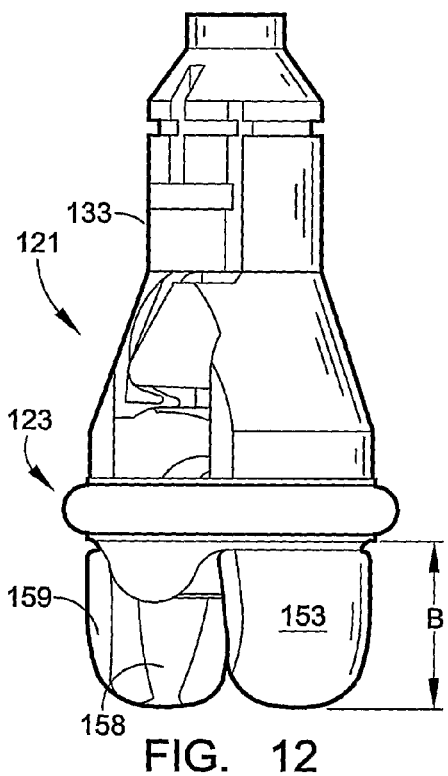
FIG. 12 is a perspective view of an assembly of an alternative embodiment of a holder-inserter shown with a valve similar to that sold by St. Jude Medical, Inc. carried thereon.
Figure 13:
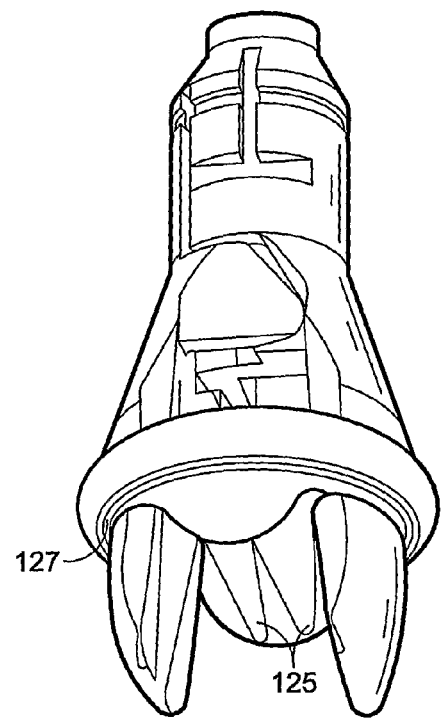
FIG. 13 is a perspective view of the assembly shown in FIG. 12 from another angle.

Basically the exterior surface of the guide members 47, 49 may be any surface curved in a plane perpendicular to longitudinal axis. It is preferably curved both in the plane perpendicular to the longitudinal axis of the heart valve inserter and in the plane parallel to the longitudinal axis, as is depicted in FIGS. 2 and 4-9; however it may be curved only in the plane perpendicular to longitudinal axis, as shown in FIGS. 10 and 11 where the surface 83 is a section of a cone. The exterior surfaces 53, which are preferably double-curved as illustrated in FIG. 4, are more preferably sections of a surface of revolution. They may be sections of a sphere or of an ovoid or any generally similar shape which might be referred to as spheroidal or ovoidal. By ovoidal is meant ellipsoidal, paraboloidal or the like, with ellipsoidal being most preferred. Although from the standpoint of symmetry it is preferable that both guide members 47 and 49 have surfaces 53 which are sections of the same surface of revolution, it should be understood that the guide members, when they are in the ultimate engaging orientation shown in FIG. 8, may not lie precisely on the same surface of revolution because their orientation may be somewhat askew with regard to each other, e.g. because of tolerances or other such factors.

As best seen in FIG. 5, at the upper ends of the guide members where the flanges 51 are located, their circular outer edges should subtend an arc of at least about 60° and more preferably an arc between about 75° and about 105°. The upper size limitation on the arc is determined by the amount of clearance which exists in the heart valve to be implanted, because as apparent from FIG. 3, the guide members need to pass between the leaflets 25 and the interior wall of the valve body 27. An arc of at least about 60° at the upper regions is felt to be sufficient to adequately spread the tissue orifice to facilitate the easy entry of the valve into position. Hollows 58 in the interior surfaces (FIG. 2) also provide clearance for the leaflets.

Side edge surfaces 59 of the guide members 47, 49, as best seen in FIGS. 5, 6 and 7, are not longitudinal but are canted; they are preferably canted at a slight angle of at least about 5° and preferably at least about 10°. Thus, as can be seen from FIGS. 5 and 6, although the respective side surfaces 59 of the guide members 47, 49 are co-planar, they do not lie in a plane parallel to the longitudinal axis, but they are offset so that there is a taper towards the longitudinal axis as these side surfaces extend toward the tips of the guide members. The flanking side edge surfaces of the guide members (which are identified in FIGS. 5 and 6 by the reference numeral 59) more easily enter the annulus because of this about 5°-10° offset; moreover, these surfaces 59 exert an outward camming action with regard to both the tissue and any pledglets being used to retain sutures on the heart side of the orifice when the holder-inserter carrying the heart valve is rotated after it has been inserted sufficiently into the excised orifice so that the guide members are in contact with the tissue.

The longitudinal length of the guide members is also considered to be important so that further insertion of the guide members, after contact with the tissue is made, exerts a relatively slow and smooth outward deflection of the tissue. In this respect, it is preferred that the longitudinal length of the guide members, i.e., the distance A in FIG. 8, should be between about 20% and about 80% of the diameter of the leading portion of the valve body, more preferably between about 30% and about 40% of the diameter of the valve body circular rim. The longer the length of the guide member, the more gradual may be the radius of curvature of the exterior surfaces which in turn results in a smoother spreading of the annulus. When the valve is close to being in its fully inserted position, it is normal that the inserter be rotated, and it is during this rotation that the side edge surfaces 59 cam outward regions of the tissue annulus that were not initially in contact with a guide member exterior surface.

It can also be seen from FIG. 5 that the edge from one corner C (FIGS. 2 and 5) of a tip to the opposite corner C would be an arc of slightly less than the arc at the upper edge of the surface at the edge of the flange 51 as a result of the canting of the side surfaces 59. Moreover, to avoid a sharp edge at the distal end, the tip ends of the guide members are flattened creating narrow flat surfaces 60. The interior surfaces of the guide members, which are recessed to provide the hollows 58 facing each other, further avoid interference with the leaflets of the bileaflet valve.

When the holder-inserter 21 is in engagement orientation with a bileaflet heart valve 23, as depicted in FIG. 7, the upper sections 39 and 43 of the two main body parts have been pivoted into abutting engagement with each other. The upper sections include an annular groove 61 about the periphery wherein a flexible tensile member 63 is routed and tied to lock them in this abutting position. The tensile member 63, usually a short length of suture cord, is preferably threaded through a transverse bore 64 in the upper section 39 and knotted. FIG. 4 shows a longitudinally extending slot 65 which facilitates the surgeon cutting the tensile member 63 to release the engagement and permit the removal of the holder-inserter after the heart valve 23 has been implanted and at least preliminarily sutured into the desired orientation in the wall of the heart.

The front portion 35 of the main body also includes a cap section 67 wherein a top cavity 69 is formed that may extend completely through the body (as indicated in FIG. 5). The upper end of the cavity 69 is shaped so as to interengage with a cooperating member formed at the distal end of a handle (not shown) as well known in this art. The holder-inserter 21 is designed such that it would be commonly packaged together with the heart valve and sterilized prior to shipment to a hospital or other facility. When ready for use, the package would be opened in the operating room, and a sterilized handle would be mated with the assembly via the cavity 69 at the upper end of the holder-inserter once the operation is ready to begin, or later when the surgeon has selected the precise size of heart valve to be implanted. During shipment, the assembly is stably supported in packaging by a C-shaped clip that is received in the pair of side slots 73 provided in the main body, as best seen in perhaps FIG. 9 and as generally known in this art.

After the leaflets of the defective natural valve have been excised by operating through the aorta, sutures are placed about the annulus, sometimes with supporting pledglets disposed on the left ventricle side of the annulus, and spaced around the circumference thereof. The surgeon would then insert the holder-inserter 21 with the engaged valve 23 so that the guide members 47, 49 extend through the annulus. This insertion movement causes the sloping surfaces 53 to engage the edge of the tissue annulus, causing it to be smoothly and slowly expanded outward and guiding entry of the leading edge of the valve body into the orifice. The surgeon then rotates the device to smoothly spread the remaining circumference of the tissue annulus outward in arcuate locations where it was not initially in contact, to align the bileaflet valve as desired with respect to the left ventricle. The rotation causes the side edges surfaces 59 not only to cam the tissue outward, but also to engage edges of any pledglets that might be located there to displace them so they will not possibly lie between the valve body exterior surface and the raw edge of the tissue. An appropriate corner blend (not shown) between the surfaces 53 and 59 is preferably included to facilitate this displacement. As a result, the engaged heart valve 23 is moved smoothly into its desired orientation with the raw edge of the tissue annulus lying in abutment against the concave, generally toroidal exterior surface of the leading edge 29 of the heart valve 23. At this time, the surgeon sutures the valve at least partially in place using curved suture needles which are passed through the sewing ring 31 and then tied off, as well known in this art. The surgeon can then cut the tensile member 63 where it passes over the cutting slot 65 so as to release the engagement at the upper end of the main body; this allows the leg 45 at the bottom of the rear part 37 to pivot freely and disengage from its contact with the interior surface of the valve body. Slight movement of the inserter to the right in FIG. 8 disengages the leg 41 from its contact; this allows the holder-inserter to be withdrawn straight away, carrying with it the cut flexible member 65 which is retained in the transverse bore 64 in the cap section.

Depicted in FIGS. 10 and 11 is an alternative embodiment of a holder-inserter wherein, instead of using guide members that have the double curved exterior surfaces, smooth sloping surfaces are provided by forming each of the guide members 81 with surface 83 which is a section of a cone. Except for this change, the guide members 81 resemble the guide members 47, 49 previously described. They have similar flat bottom tips 85 which have outer edges that are similarly spaced apart and oriented as described above.

Illustrated in FIGS. 12-15 is an alternative embodiment of a holder-inserter 121 which is designed to support a different mechanical heart valve; it is shown as carrying a mechanical heart valve of the general type as has been sold for several decades by St. Jude Medical, Inc. The components of the holder-inserter 121 are given reference numerals the same as the holder-inserter 21 plus 100. Accordingly, it should be understood that statements made earlier with respect to such a corresponding part are equally applicable to the part bearing the corresponding reference numeral in FIGS. 12-15.

This alternative embodiment of the device 121 that is shown is proportioned and shaped to facilitate the implantation of a mechanical heart valve 123, similar to that which is marketed by St. Jude Medical, Inc. and shown in U.S. Pat. No. 4,276,658. This valve 123 likewise employs a pair of leaflets 125 that are pivotally mounted on a valve body or orifice ring 127. The illustrated valve 123 is designed to be inserted as an aortic valve replacement where it will be positioned so that a pair of semicircular extensions 128 at its entrance end protrude toward the left ventricle in the annulus from which leaflets of the defective natural valve were excised. The implanted prosthesis is secured in place by suturing through a sewing ring 131 which is affixed to a central exterior region of the valve body 127, with sutures being secured by pledgets which are positioned on the heart side of the annulus, i.e. facing the left ventricle of the heart.

The holder-inserter device 121 has a main body 133 which comprises two hinged, relatively movable parts, a front part 135 and a rear part 137. The front or left hand part 135 (as oriented in FIG. 14) is formed with an upper section 139 and a depending leg 141. The rear or right hand part 137 is formed with an upper section 143 and a depending leg 145. The two legs 141 and 145 have the same construction, being mirror images of each other, with a pair of integral, sloping guide members 147, 149 being located at their lower ends. Each guide member has a transverse surface or a flange 151 formed at its upper end against which the entrance end 129 of the valve seats, in the groove provided in the legs 141, 145; this end is the leading edge of the heart valve during implantation from the aorta. Engagement in the groove secures the valve in place on the holder-inserter 121 when the two body parts 135, 137 are in the engaging orientation, as depicted in the drawings.

Figure 14:
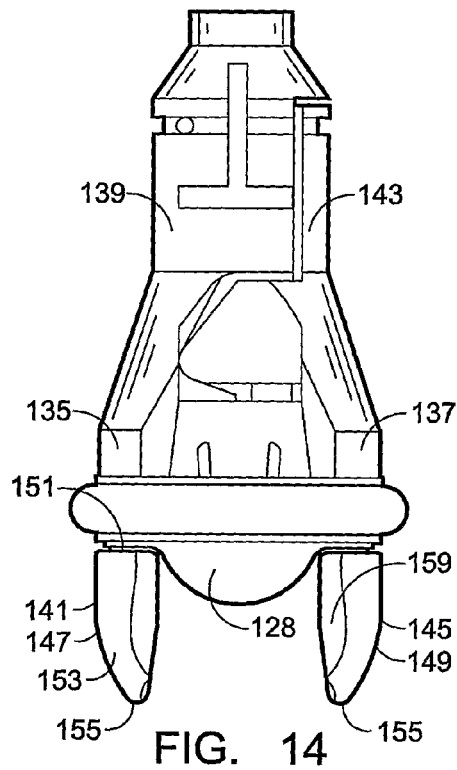
FIG. 14 is a front view of the assembly shown in FIG. 12.
Figure 15:
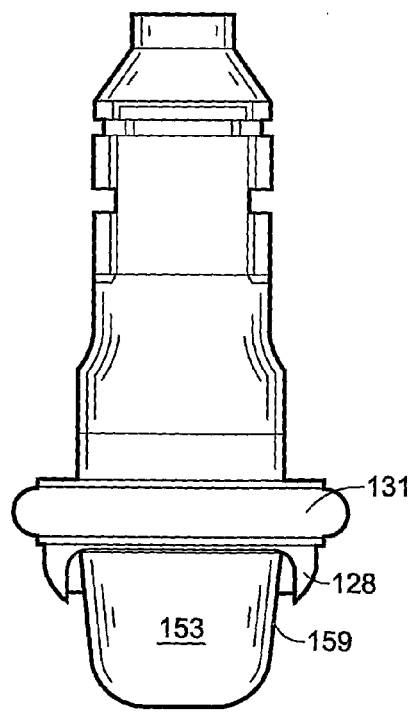
FIG. 15 is a side view of the assembly shown in FIG. 14.

A sloping exterior surface 153 of the guide member 147 smoothly extends from the outer edge of the flange 151 down to a tip 155. When the two legs 141, 145 are in their engaging position, the outer edge of the transverse surface 151 lies close to the outer edge of the rim of the heart valve entrance end 129. The longitudinally sloping surface 153 extends smoothly as a continuous curve over the entire distance from the edge of the ledge to the lower or bottom tip 155. As best seen in FIG. 14, the outer edges of the tips 155 are again spaced apart at a distance which is substantially less than the outer diameter of the rim 129 of the heart valve.

The upper ends of the guide members where the flanges 151 are located have circular outer edges that again each subtend an arc of about 75° and about 105°. Hollows 158 in the interior surfaces also provide clearance for the leaflets.

Side edge surfaces 159 of the guide members 147, 149 are again preferably canted at a slight angle of at least about 5° and preferably at least about 10°. Again, the preferred longitudinal length of the guide members, i.e., the distance B in FIG. 12, should be between about 20% and about 80% of the diameter of the leading edge of the valve body 127, more preferably between about 30% and about 40% of the diameter of the outer circular rim surface of the valve body 127.

The remainder of the construction of the holder-inserter 121, primarily the upper portion thereof, is the same as that hereinbefore described for the holder-inserter 21. The bileaflet heart valve 123 would be installed and released in the manner described hereinbefore. Similarly, the surgeon would insert the holder-inserter 121 with the valve 123 carried thereon so that the sloping guide members 147, 149 extend through the annulus from which the defective leaflets of the natural valve have been excised. Again, the sloping surfaces 153 would cause the edges of the tissue annulus to be smoothly and slowly expanded outward, guiding the entry of the leading edge of the valve body 127 into the orifice. Then, the surgeon would rotate the device to smoothly spread the remaining circumference of the tissue annulus outward, and to align the bileaflet valve as desired with respect to the left ventricle. Once the desired, correct orientation has been attained, the surgeon would suture the valve at least partially in place and then, as earlier described, cut a tensile member to release the engagement at the upper end of the main body of the two portions of the holder-inserter, allowing the leg 145 at the bottom of the rear part 137 to pivot freely and disengage so that the holder-inserter 121 can be withdrawn straightaway.

Thus, it should be appreciated that a holder-inserter for a mechanical heart valve prosthesis has been provided that fully meets the objectives stated above. However, although preferred embodiments have been illustrated and described, which constitute the best mode presently known to the inventors for carrying out this invention, it should be appreciated that various changes and modification as would be obvious to one having the ordinary skill in this art may be made without departing from the scope of the invention which is defined in the claims appended hereto. In this respect, although the description has been directed to the implantation of an aortic heart valve, it should be understood that similar advantages are obtained when the holder-inserter is used to insert a valve in the mitral position, for example. The disclosures of all of the previously enumerated U.S. patents are expressly incorporated herein by reference.

Particular features of the invention are emphasized in the claims which follow.

The invention claimed is:

1. A prosthetic heart valve holder to insert a prosthetic heart valve into an annulus of the heart of a patient from which the patient's defective valve leaflets have been excised, which holder comprises:

a main body which includes two legs that are shaped and oriented to pass axially through a prosthetic heart valve having a leading portion of substantially circular cross section and are proportioned to releasably engage with the valve, said legs each having a groove formed in the exterior surface thereof shaped and sized to receive the valve and releasably engage the leading portion of the valve;

said main body having a connector corresponding to a handle to move and position the main body together with the valve releasably engaged therewith;

portions of said legs protruding longitudinally past the valve carried thereon in the groove and terminating in two sloping guide members which have (1) leading tips that are diametrically spaced apart a distance less than the diameter of the leading portion and (2) trailing transverse surfaces at the upper ends of the sloping guide members that form a boundary of the groove against which the leading portion seats; and said guide members having radially outward-facing surfaces that are generally surfaces of revolution that smoothly slope from said leading tips outward towards radially outward arcuate edges which lie at a diameter about equal to the leading portion, and each of said guide members having a longitudinal length extending from said trailing transverse surface to said leading tip, which length is between about 30% and about 80% of the diameter of the leading portion;

wherein said main body has a longitudinal axis that substantially coincides with a longitudinal axis of the valve and wherein said outward-facing surfaces of said guide members are smoothly curved in a plane perpendicular to said longitudinal axis;

wherein said main body comprises two hinged parts and pivoting of one leg relative to the other leg causes one guide member to be moved toward the other guide member to release the valve releasably carried thereon;

whereby passage of the leading portion into the annulus is facilitated by the presence of said guide members which spread the annulus and guide the valve into the annulus.

2. The holder of claim 1 wherein said guide member outward-facing surfaces are generally sections of a sphere or of an ovoid.

3. The device holder of claim 1 wherein said guide member outward-facing surfaces are generally sections of an ellipsoid.

4. The holder of claim 1 wherein the radially outward arcuate edges each include an arc of at least 60°.

5. The holder of claim 1 wherein said guide member outward-facing surfaces are also curved in a plane parallel to said longitudinal axis.

6. The holder of claim 1 wherein said guide member tips terminate in generally circular leading edges, which edges are arcs of a circle having a diameter generally less than 65% of an outer diameter of the leading portion.

7. The holder of claim 1 wherein each sloping guide member includes an inner surface having a hollowed cavity portion configured to accommodate a leaflet of the valve.

8. The holder of claim 1 wherein each sloping guide member includes an outer surface, connected to one of the outward-facing surfaces, canted at an angle of at least four degrees.

* * * * *